United States Patent [19]

White

[11] Patent Number: 5,297,431
[45] Date of Patent: Mar. 29, 1994

[54] AUTOMATED SAMPLE DILUTION

[75] Inventor: Landy B. White, Sunol, Calif.

[73] Assignee: Thermo Separation Products (California) Inc., Fremont, Calif.

[21] Appl. No.: 891,703

[22] Filed: Jun. 1, 1992

[51] Int. Cl.⁵ .......................................... G01N 35/06
[52] U.S. Cl. .......................................... 73/864.22
[58] Field of Search ................. 73/864.21–864.25, 73/864.81, 864.83–864.85, 864.87, 863.72, 863.73, 864.22; 422/70, 63, 81–82.13, 100

[56] References Cited

U.S. PATENT DOCUMENTS

| | | |
|---|---|---|
| 2,797,149 | 6/1957 | Skeggs . |
| 2,879,141 | 3/1959 | Skeggs . |
| 3,028,224 | 4/1962 | Ferrari, Jr. . |
| 3,072,442 | 1/1963 | Ferrari . |
| 3,097,927 | 7/1963 | Skeggs . |
| 3,186,235 | 6/1965 | Ferrari . |
| 3,193,358 | 7/1965 | Baruch . |
| 3,334,018 | 8/1967 | Smythe . |
| 3,512,936 | 5/1970 | Clements . |
| 3,551,063 | 12/1970 | Smythe et al. . |
| 3,647,187 | 3/1972 | Dannewitz . |
| 3,695,281 | 10/1972 | Leon . |
| 3,804,593 | 4/1974 | Smythe et al. . |
| 3,811,841 | 5/1974 | Kassel . |
| 3,827,303 | 8/1974 | Shiina ............ 73/864.84 |
| 3,840,438 | 10/1974 | Ast et al. . |
| 4,004,451 | 1/1977 | Burns . |
| 4,130,394 | 12/1978 | Negersmith ............ 422/82 |
| 4,418,039 | 11/1983 | Adler . |
| 4,478,095 | 10/1984 | Bradley et al. . |
| 4,517,302 | 5/1985 | Saros . |
| 4,523,484 | 6/1985 | Kadota et al. .......... 73/864.22 |
| 4,526,754 | 7/1985 | Burns et al. . |
| 4,622,457 | 11/1986 | Bradley et al. . |
| 4,713,974 | 12/1987 | Stone . |
| 4,792,434 | 12/1988 | Metzger et al. . |
| 4,823,622 | 4/1989 | Nohl et al. . |
| 4,836,037 | 6/1989 | Nohl et al. . |
| 4,853,336 | 8/1989 | Saros et al. . |
| 4,859,605 | 8/1989 | Metzger et al. . |
| 4,957,009 | 9/1990 | Nohl et al. . |
| 5,101,673 | 4/1992 | Uffenheimer et al. . |
| 5,158,748 | 10/1992 | Obi et al. ................ 422/100 |

Primary Examiner—Robert Raevis
Attorney, Agent, or Firm—Kilworth, Gottman, Hagan & Schaeff

[57] ABSTRACT

A sample preparation method and apparatus is provided which is capable of automatic operation over a broad range with improved accuracy and precision, and which is capable of sampling with improved accuracy and flushing without operator intervention. A pair of syringes are used to measure large and small volumes of components, respectively, and can be operated automatically using a processor to prepare samples. Further, the method and apparatus incorporate a solvent selector valve which permits various solvents to be selected as required to prepare a particular sample. Automatic flushing of the apparatus is also provided after the preparation of each sample.

25 Claims, 1 Drawing Sheet

AUTOMATED SAMPLE DILUTION

BACKGROUND OF THE INVENTION

This invention relates to the automatic preparation of samples in vials or containers. More particularly, the invention relates to the automatic preparation of liquid samples in vials for use in a chemical analysis system.

Automation of chemical analyses which were once performed by hand has progressed significantly. In the field of liquid chromatography, a number of automated chromatographic analysis systems are currently commercially available. These systems, referred to as autosamplers, aid in the automation of chromatographic analysis by storing a number of individual samples and injecting them sequentially into a chromatograph for analysis. The chromatographic analysis, which typically takes between about 10 and 60 minutes, can be completed without human intervention.

Autosampler systems typically use trays of sample-containing vials of a small volume (e.g. 1.5–1.8 ml) which are fabricated of glass. The vials may be sealed with a flexible septum held onto the top of the vial by a cap with a hole in the center thereof. The hole exposes a portion of the rubber septum to a hollow needle which is pushed through the septum and into the sample.

Suction and/or pressure is used withdraw a predetermined amount of the sample through the needle, and the sample is then injected into the chromatograph. In early autosamplers, a syringe was used to withdraw the sample by suction into a sample loop, and then used to discharge the sample therefrom by pressure for analysis. It is a common problem in all autosamplers that the accuracy of sample delivery may be affected by loss of sample in wetting the sides of the sample loop, and the precision with which samples are obtained may be similarly limited by the syringe, which is sized to handle both large and small volumes.

Currently, additional demands are being placed on such autosampler systems to increase further the automation of the chemical analyses. In addition to automated sampling there is the desire to produce systems capable of some sample preparation. For example, there may be a need to dilute the sample before analysis or to add a reagent to aid in sample detection. Some reagents may take several minutes to react and may require continuous mixing and/or heating at elevated temperatures. As this time is comparable to the time required for chromatographic analysis, it may be desirable to have more than one sample in process at one time. It may also be necessary to remove a sample from the tray and perform an operation on it such as mixing or heating, or simply to provide the sample to one of various analysis stations.

Autosamplers of more recent vintage still perform the same basic tasks, but incorporate various apparatus and method improvements to improve sampling precision and accuracy, and to increase the capability for sample preparation. For example, Nohl et al, U.S. Pat. No. 4,957,009 (the '009 patent) discloses a pushloop liquid sampling method for an existing sampling apparatus which improves accuracy of sample delivery by eliminating mechanical backlash in the syringe drive mechanism. Stone, U.S. Pat. No. 4,713,974 (the '974 patent) shows a variety of improvements in an autosampler apparatus which increase its capability for preparing samples and quickly flush or prime the lines. However, the need for manual priming and solvent delivery in accordance with the '974 patent, prevents automatic operation. As well, it remains a problem in both the '974 and '009 patents that the accuracy of sample delivery may be affected by loss of sample in wetting the sides of the sample tube, and the precision with which samples are obtained may be limited by the syringe size The '974 patent suggests manual interchange of syringes having different capacities to change the capacity, precision and accuracy of sample preparation. However, the need for operator intervention to perform such procedures again inhibits truly automatic sample preparation.

Accordingly, there is a need in the art for an autosampler which is capable of automatic operation to provide sample preparation with improved accuracy and precision.

SUMMARY OF THE INVENTION

The present invention meets that need by providing a sample preparation method and apparatus which is capable of automatic operation over a broad range of sample size with improved accuracy and precision, and which is capable of sampling with improved accuracy and flushing without operator intervention. The present invention uses both a large and small volume syringe to measure and deliver large and small volumes of component samples, respectively, and can be operated automatically using a processor means to prepare samples. Further, the method and apparatus incorporate a solvent selector valve which permits various solvents to be selected as required to prepare a particular sample.

In accordance with one aspect of the present invention, an apparatus for automatic preparation of samples from a plurality of components is provided comprising a solvent selector valve and a flush valve interconnected with the solvent selector valve, a large volume solvent syringe, and a smaller volume sample syringe connected to the flush valve. The solvent syringe and sample syringe are operable by first and second drive motors. A sample line extends from a port of the flush valve with a needle disposed at the end of the sample line for insertion into a container, and means for positioning are further provided to sequentially position ones of a plurality of containers or vials at the needle. Finally, the apparatus includes processor means for controlling the operation of the solvent selector valve, flush valve, solvent syringe, sample syringe, and the means for positioning, to automatically prepare a sample in a container. The processor means is preferably programmable.

The apparatus of the present invention may be provided independently of an analysis system to provide just sample preparation, or may be incorporated into an analysis system with an analysis device. The sizes of the lines, valves and syringes in the apparatus will, thus, depend on the sample size required for a particular analysis device. However, in accordance with the preferred embodiment, the volume of the solvent syringe is preferably at least 10 times the volume of the sample syringe. Thus, for example, where the analysis system includes a liquid chromatograph, the volumes of the solvent syringe and sample syringe are in a ratio of at least 10:1, and preferably selected from within the range of 50 microliters to 50 milliliters.

In a preferred embodiment of the invention the solvent syringe is connected to a port of the flush valve, such that the solvent syringe communicates through the flush valve with the main port of the solvent selector valve, when the flush valve is in a first position. Connecting the flush valve and the main port of the solvent selector valve is a solvent loop whose volume is greater than that of the solvent syringe. The solvent loop allows selected solvents to be withdrawn through the solvent selector valve by the solvent syringe without contaminating the solvent syringe, reducing later efforts required to purge the system for the next sample preparation.

In the preferred embodiment, the flush valve, in a first position, is used in conjunction with the solvent selector valve to connect the solvent syringe to the sample line, and move larger, measured amounts of fluids therethrough. Further, the flush valve in a second position is used to connect the smaller sample syringe to the sample line, allowing smaller, measured amounts of fluids to be moved thereby. Improved precision and accuracy in the drawing and delivery of fluids is obtained by so using the two syringes.

In a preferred embodiment, the apparatus includes an injection valve, such as a six port, two-position valve, to permit amounts of a prepared sample to be withdrawn and injected into an analysis device. Again, however, it is understood that the present invention may be used independently for sample preparation, or incorporated into an analysis device.

In a preferred embodiment, the apparatus further includes a flush solvent reservoir and a flush solvent line connecting the reservoir to the flush valve to allow the entire apparatus to be flushed after each sample is prepared, to ready the apparatus for the next sample to be prepared.

In accordance with another aspect of the present invention, a method for automatically preparing a sample from a plurality of components is provided which uses the apparatus described above, and comprises the steps of switching the solvent selector valve from an initial position to select a solvent, drawing solvent from a solvent reservoir through the solvent selector valve in a first direction with the solvent syringe, thereafter switching the solvent selector valve to the first position, and injecting solvent with the solvent syringe in a second direction through the solvent selector valve, the flush valve, the injection valve, and up through a needle, with the flush valve and injection valve in respective first positions. Using the larger volume solvent syringe, these steps purge the sample line with the selected solvent.

The method next calls for switching the flush valve to a second position to connect the needle to the sample syringe, positioning a component reservoir at the needle, and drawing a component sample from the component reservoir through the needle in the first direction with the sample syringe. These steps provide for a sample of the component positioned at the needle to be drawn into the sample line. Typically, component samples are small, and use of the smaller sample syringe permits increased accuracy and precision in sample preparation. These steps may be performed once or repeatedly, as needed, to draw quantities of various components into the sample line. Whenever drawing solvents or other component samples, it is preferred to separate the individual components with air bubbles to prevent premature or undesirable mixing.

Once the desired components are drawn into the sample line, the method next calls for the steps of removing the component reservoir from the needle, positioning a container at the needle, switching the flush valve to the first position, and injecting both the component sample and a predetermined amount of the solvent with the solvent syringe through the needle in the second direction and into the container. Delivery of the solvent in this manner serves to flush the other component samples from the sample line into the container, providing more accurate delivery of the component samples. A sample reservoir having a plurality of components is thereby automatically prepared in the container.

Where it is desired for the sample which has been prepared to further be analyzed, the method may further include the steps of switching the flush valve to the second position, drawing a test sample from the sample reservoir through the needle and past the injection valve in the first direction with the sample syringe, switching the injection valve to a second position, injecting a portion of the test sample into the injection valve in a second direction with the sample syringe, switching the injection valve to the first position, and injecting the portion of the test sample into an analysis device. These additional steps permit the sample which has been prepared to, in turn, be tested. The small syringe is used to provide accurate withdrawal of the test sample.

Accordingly, it is an object of the present invention to provide a sample preparation apparatus and method which is capable of automatic operation with improved accuracy and precision. This, and further objects and advantages of the present invention will become apparent from the following detailed description, the accompanying drawings, and the appended claims.

DETAILED DESCRIPTION OF THE PREFERRED EMBODIMENT

Figure 1:
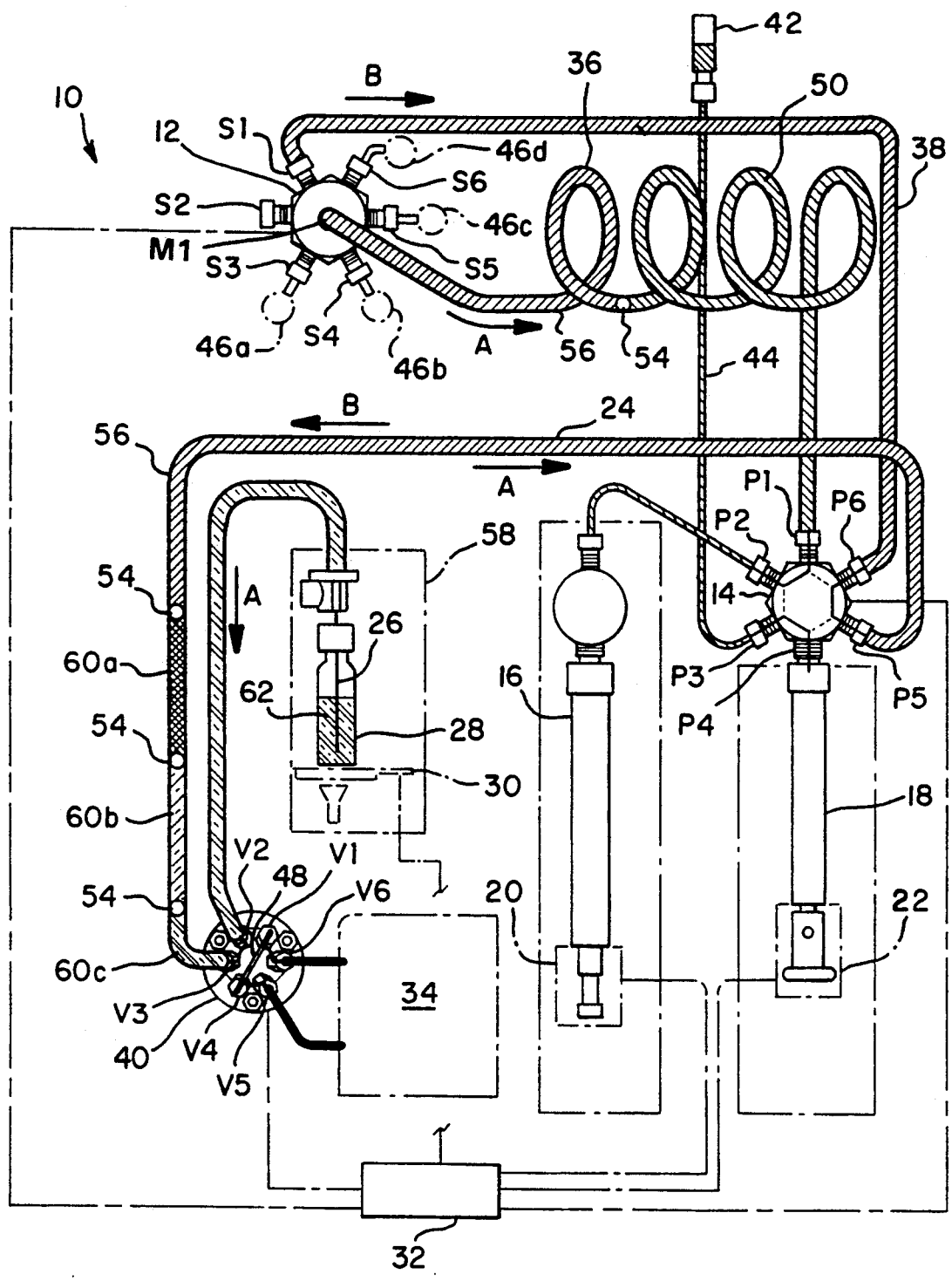
FIG. 1 is a schematic diagram of the sample preparation apparatus of the present invention.

Referring to FIG. 1, in accordance with one aspect of the present invention, an apparatus 10 for automatic preparation of samples from a plurality of components is provided comprising a solvent selector valve 12 and a flush valve 14 interconnected with the solvent selector valve 12, a large volume solvent syringe 16, and a smaller volume sample syringe 18 connected to the flush valve 14. The solvent syringe 16 and sample syringe 18 are operable by first and second drive motors 20 and 22, respectively, shown schematically in FIG. 1, and generally available commercially. A sample line 24 extends from a port P5 of the flush valve 14 with a needle 26 disposed at the end of the sample line 24 for insertion into a container 28, and means 30 for positioning are further provided to sequentially position ones of a plurality of containers 28 or vials at the needle 26. The precise means 30 for positioning used to position the container 28 at the needle 26 is not critical to the present invention, and any means known in the art may be used, such as that shown by the '974 patent, or as shown by Bradley et al., U.S. Pat. No. 4,622,457, assigned to the assignee of the present invention. Means 30 for positioning are, thus, shown schematically and representatively as a platform in FIG. 1. It is preferred to move the container 28 up to receive the needle 26, but other means 30 for positioning which move the needle 26 into the container 28 can also be used. Finally, the apparatus 10 includes processor means 32 for controlling the operation of the solvent selector valve 12, flush valve 14, solvent syringe 16, sample syringe 18, and the means 30 for positioning, to automatically prepare a sample in a container 28. The processor means 32 is preferably programmable. The apparatus 10 of the present invention may be provided independently of an analysis system to provide just sample preparation, or may be incorporated into an analysis system including an analysis device 34, such as a liquid chromatograph. While the volumes of the solvent syringe 16 and the sample syringe 18 will depend on the sample size required for the analysis device 34 used in a particular application, the volume of the solvent syringe 16 is preferably at least 10 times the volume of the sample syringe 18. Thus, for example, where the analysis device 34 is a liquid chromatograph, the volumes of the solvent syringe 16 and sample syringe 18 are preferably within the range of 50 microliters to 50 milliliters, and most preferably within the range of 50 microliters to 5 milliliters.

In the preferred embodiment of the invention shown in FIG. 1, the solvent syringe 16 is connected to a port P2 of the flush valve 14, such that the solvent syringe 16 communicates through port P1 of the flush valve 14 with the main port M1 of the solvent selector valve 12, when the flush valve 14 is in a first position. In FIG. 1, the solid line connecting adjacent ports of the flush valve 14 demonstrate the first position of the valve, while the dashed lines show the second position. Connecting the flush valve 14 and the main port M1 of the solvent selector valve 12 is a solvent loop 36 whose volume is greater than that of the solvent syringe 16. The volume of the solvent loop 36 allows selected solvents to be withdrawn through the solvent selector valve 12 by the solvent syringe 16 without contaminating the solvent syringe 16, reducing later efforts required to purge the apparatus 10 for the next sample preparation. As further seen in FIG. 1, a transfer line 38 extends from port P6 of the flush valve 14 to the port S1 of the solvent selector valve 12.

In the preferred embodiment, the flush valve 14, in the first position shown, is used in conjunction with the solvent selector valve 12, also in a first position, to connect the solvent syringe 16 to the sample line 24 to move large, measured amounts of fluids through sample line 24. In its first position, solvent selector valve 12 connects port S1 to port M1, in its second position connects port S2 to port M1, and so on, for, preferably, six positions corresponding to ports S1 through S6.

The sample syringe 18 is also used to move fluids in sample line 24. With the flush valve 14 in a second position, the smaller sample syringe 18 is connected to the sample line 24, allowing smaller, measured amounts of fluids to be moved thereby. Improved precision and accuracy in the drawing and delivery of fluids is obtained by so using the two syringes, solvent syringe 16 and sample syringe 18, for drawing and injecting large and small volumes, respectively. The solvent selector valve 12 is preferably at least a four position selector valve, and more preferably a standard six port, six position valve. The flush valve 14 is preferably a two-position, six port valve, such as are available from many sources including Valco, Scientific Systems, Inc., Rheodyne, and Hamilton (Reno, Nev.).

In a preferred embodiment, the apparatus 10 includes an injection valve 40, such as a six port, two-position valve, to permit amounts of a prepared sample to be withdrawn and injected into an analysis device 34. Injection valve 40 is positioned in sample line 24, as shown in FIG. 1, with two ports V2 and V3 connected to the sample line 24. The injection valve 40 is preferably a high pressure valve, and includes a sample loop 48 extending between two ports V1 and V4 of the injection valve 40. The two remaining ports V5 and V6 are dedicated for connection to an analysis device 34. In FIG. 1, the solid lines connecting adjacent ports of the injection valve 40 demonstrate the first position of the valve, wherein the sample line 24 remains connected to itself, and the ends of the sample loop 48 are connected to ports V5, V6. For clarity, the second position is not shown, but it is understood that in the second position other adjacent ports will be connected so that the sample line 24 is connected to the ends of the sample loop 48 and the two ports V5, V6 dedicated for connection to an analysis device 24 are connected to each other. Alternatively, the injection valve 40 may be part of an analysis device 34, and the injection valve 40 may be connected to the apparatus 10, as shown.

In a preferred embodiment, the apparatus 10 further includes a flush solvent reservoir 42 and a flush solvent line 44 connecting the flush solvent reservoir 42 to the flush valve 14 to allow the entire apparatus 10 to be flushed after each sample is prepared and ready the apparatus 10 for the next sample to be prepared.

In accordance with another aspect of the present invention, a method for automatically preparing a sample from a plurality of components is provided which uses the apparatus 10 described above and shown in FIG. 1. The method may be illustrated by further reference to FIG. 1.

In accordance with the present method, the apparatus 10 in its initial state includes flush solvent 50 in all lines 24, 36 and 38, and syringes 16, 18, and has all valves 12, 14 and 40 switched to their respective first positions. As a first step, the solvent selector valve 12 is switched to select a solvent from one of the solvent reservoirs 46a-46d, and then the solvent syringe 16 is used to draw a volume of solvent from one of the plurality of solvent reservoirs into solvent loop 36 in a first direction A. The volume of solvent drawn preferably includes both the volume of solvent to be included in a sample, as well as a volume, at least as great as the dead volume of the apparatus 10, which is needed to deliver the solvent into a container 28. More specifically, in accordance with the preferred method, the solvent selector valve 12 is first switched to a second position to connect the top main port M1 to port S2, which is connected to air. The solvent syringe 16 is then retracted slightly to draw an air bubble 54 into the solvent loop 36. The solvent selector valve 12 is switched to connect the solvent loop 36 to one of the solvent reservoirs 46a-46d at ports S3-S6, and then the solvent syringe 16 is used to draw the selected solvent 56 into the solvent loop 36 in first direction A. The volume of the solvent loop 36 is greater than that of the solvent syringe 16, so that the air bubble 54 which separates the selected solvent 56 from the flush solvent 50 never enters the solvent syringe 16, and a selected solvent 56 never contaminates the solvent syringe 16.

With the flush valve 14 remaining in its first position (so that pairs of ports P1 and P2, P3 and P4, and P5 and P6 communicate, respectively), the solvent selector valve 12 is again switched to the second position. The solvent syringe 16 is retracted to form another air bubble (not shown) in the solvent loop 36. Thereafter, the solvent selector valve 12 is switched to the first position connecting M1 and S1, and the solvent syringe 16 is advanced to push the selected solvent 56 in a second direction B through the transfer line 38, flush valve 14, sample line 24 and needle 26 to purge the flush solvent 50 therefrom. The flush solvent 50 purged from the apparatus 10 is received at the sample station 58 in a trough (not shown) which carries it to waste.

In accordance with the preferred method, the injection valve 40 remains positioned in a first position, as shown in FIG. 1, during this step of purging.

Still referring to FIG. 1, in accordance with the method of the present invention, one or more component samples 60a, 60b, 60c . . . may next be drawn into the sample line 24 in first direction A through the needle 26 from component reservoirs in containers 28 at the sample station 58. The flush valve 14 is first switched to its second position so that ports P4 and P5 communicate through the flush valve 14, and so that sample syringe 18 communicates with sample line 24. More specifically, in the preferred embodiment, the step of drawing a component sample 60a, 60b, 60c into the sample line 24 is performed with no container 28 at the needle 26, by retracting the sample syringe 18 slightly to draw an air bubble 54 in a first direction A into the sample line 24, positioning a component reservoir (in a container 28) at the needle 26 with the means 30 for positioning, and retracting the sample syringe 18 to withdraw the desired amount of the component sample into the sample line 24 in first direction A.

Once the desired volume of the component is drawn by the sample syringe 18, the container 28 is removed. These steps may be repeated and the sample syringe 18 may be used to draw additional bubbles 54 and components, as shown, from additional sample containers 28 brought to the sample station 58 in like fashion. Preferably, each component sample 60a, 60b, 60c . . . drawn using the sample syringe 14 is separated by an air bubble 54, as shown in FIG. 1 to prevent mixing. Three components 60a-60c are shown for illustration, however, one or more component samples can be drawn as needed.

Once the component samples 60a, 60b, 60c . . . are drawn into the sample line 24, a container 28 may be brought to the sample station 58 and positioned at the needle 26 to serve as a sample reservoir 62. The flush valve 14 is then switched to the first position so that once again the solvent syringe 16 is connected to the sample line 24. Solvent syringe 16 is then advanced an amount which delivers the one or more components 60a, 60b, 60c . . . and a predetermined amount of the selected solvent 56 into container 28. It is understood that the selected solvent 56 is also a component of the sample prepared.

In this manner, the components required to prepare a sample, may be automatically withdrawn and combined to form a sample reservoir 62 in a container 28. It is also possible in accordance with the present method to deliver only volumes of one or more component samples 60a, 60b, 60c to the container 28 without a selected solvent 56. In this case, the sample syringe 18 could be used instead of the solvent syringe 16 for precise delivery of the component samples. However, when a selected solvent 56 is combined with other component samples 60a, 60b, 60c . . . , the selected solvent 56 helps assure accurate delivery thereof by flushing amounts of the components wetting the walls of the sample line 24 into the container 28.

In accordance with this method, the present invention is capable of performing precise small volume sample dilutions in the range of 1:3 through 1:1500, on volumes of approximately 1.5 milliliters (ml) or less. As well, larger volume dilutions can be performed with appropriate sizing of the lines, valves and syringes. It is preferred, for best precision, however, to perform dilutions which are in the range of 1:150. Where larger dilutions are performed, precision can be improved still further by using a sample syringe 18 whose volume is much more than 10 ten times smaller than the solvent syringe 16. Where only slight dilutions are performed, for example in the range of 1:3 to 1:10, it is possible to also use the solvent syringe 16 (with the flush valve 14 in its first position) to draw component samples from sample reservoirs through needle 26.

When the present apparatus 10 is applied for use with an analysis device 34, such as a liquid chromatograph, the method further includes the steps of drawing a test sample from the sample reservoir, and injecting at least a portion of the test sample into the analysis device 34. The step of drawing a test sample from the sample reservoir may be performed by any suitable method known in the art which injects at least a portion of the test sample into the sample loop 48. For precision it is preferred, more specifically, that the test sample be withdrawn by switching the flush valve 14 to its second position so that the sample syringe 18 communicates with the sample line 24, drawing a test sample from the sample reservoir through the needle 26 and past the injection valve 40 in the first direction A with the sample syringe 18, switching the injection valve 40 to its second position to connect the sample loop 48 to the sample line 24, injecting a portion of the test sample in a second direction B into the sample loop 48 with the sample syringe 18, switching the injection valve to its first position to connect the sample loop 48 to the analysis device 34, and injecting the portion of the test sample in the sample loop 48 into the analysis device 34.

It is preferred in accordance with the method of the present invention to perform the step of drawing a test sample from the sample reservoir by first withdrawing the needle 26 from the sample reservoir, retracting the sample syringe 18 to produce an air bubble 54, and thereafter inserting the needle 26 into the sample reservoir, and removing a test sample from the sample reservoir.

In accordance with the preferred method, after preparation of each sample the container 28 in which the sample reservoir was prepared is removed from the sample station 58, and the selected solvent 56 is flushed from apparatus 10 in second direction B with flush solvent 50. With the flush valve 14 in its second position, the solvent syringe 16 is used to alternately draw flush solvent 50 from the flush solvent reservoir 42 and, with the flush valve switched to its first position, inject it in second direction B into and through the solvent loop 36, transfer line 38, sample line 24 and needle 26. With the flush valve in its first position, the sample syringe 18, is used in like fashion to draw flush solvent 50 thereinto from flush solvent reservoir 42 to flush selected solvent 56 from the sample syringe 18 into the sample line 24 in second direction B. Flushing the sample syringe 18 may require drawing several cycles of flush solvent 50 thereinto. The sample syringe 18 is preferably flushed first, after which the solvent syringe 16 is used to flush the apparatus 10 as a whole.

While certain representative embodiments and details have been shown for purposes of illustrating the present invention, it will be apparent to those skilled in the art that various changes in the apparatus and method disclosed herein may be made without departing from the scope of the invention, which is defined in the appended claims.

What is claimed is:

1. A method for automatically preparing a sample from a plurality of components by means of an apparatus including a solvent syringe and a sample syringe which has a smaller volume than the solvent syringe, a flush valve having two positions, and a solvent selector valve having a plurality of positions, said method comprising the steps of:

switching the solvent selector valve from a first position to select a solvent, and drawing solvent from a solvent reservoir through said solvent selector valve in a first direction with the solvent syringe;

switching said solvent selector valve to said first position, and injecting said solvent with the solvent syringe in a second direction through said solvent selector valve, the flush valve, and up through a needle, with said flush valve in said first position;

switching said flush valve to a second position to connect said needle to said sample syringe;

positioning a component reservoir at said needle, and drawing a component sample from said component reservoir through said needle in said first direction with said sample syringe;

removing said component reservoir;

positioning a container at said needle;

switching said flush valve to said first position;

injecting said component sample and a predetermined amount of said solvent with said solvent syringe through said needle in said second direction into said container;

whereby a sample reservoir having a plurality of components is automatically prepared in said container.

2. The method of claim 1 wherein said step of drawing solvent from a solvent reservoir through said solvent selector valve in a first direction with the solvent syringe comprises:

switching said solvent selector valve to a second position connected to air;

drawing an air bubble through said solvent selector valve in said first direction with said solvent syringe;

switching said solvent selector valve from said second position to the position corresponding to the solvent selected; and removing a volume of the solvent selected from said solvent reservoir through said solvent selector valve in a first direction with said solvent syringe.

3. The method of claim 2 wherein, after said step of removing a volume of the solvent selected from said solvent reservoir through said solvent selector valve in a first direction with said solvent syringe, said method further includes the steps of:

switching said solvent selector valve to a second position connected to air; and drawing an air bubble through said solvent selector valve in said first direction with said solvent syringe.

4. The method of claim 1 wherein said step of drawing a component sample from said component reservoir through said needle in said first direction with said sample syringe comprises:

drawing an air bubble into said needle in said first direction with said sample syringe;

inserting said needle into said component reservoir; and removing a component sample from said component reservoir through said needle in said first direction with said sample syringe.

5. The method of claim 1 wherein said solvent syringe connects to said flush valve, such that said solvent syringe performs said steps of drawing a solvent from a solvent reservoir in a first direction, and injecting said solvent in a second direction, by exerting hydraulic forces through said flush valve.

6. The method of claim 1 further comprising the step of repeating, for at least one other component reservoir, said steps of: positioning a component reservoir at said needle; drawing a component sample from said component reservoir through said needle in said first direction with said sample syringe; and removing said component reservoir.

7. The method of claim 1 wherein said apparatus includes an injection valve having two positions, and said step of injecting said solvent with the solvent syringe in a second direction through said solvent selector valve and flush valve, further injects said solvent through said injection valve which is in a first position.

8. The method of claim 7 further comprising the steps of:

switching said flush valve to a second position;

drawing a test sample from said sample reservoir through said needle and past said injection valve in said first direction with said sample syringe;

switching said injection valve to a second position;

injecting a portion of said test sample into said injection valve in a second direction with said sample syringe;

switching said injection valve to said first position, and injecting said portion of said test sample into an analysis device.

9. The method of claim 8 wherein said step of drawing a test sample from said sample reservoir comprises the steps of:

withdrawing said needle from said sample reservoir;

drawing an air bubble into said needle in said first direction with said sample syringe;

inserting said needle into said sample reservoir; and removing a test sample from said sample reservoir through said needle and past said injection valve in said first direction with said sample syringe.

10. The method of claim 7 wherein said flush valve is connected to a flush solvent reservoir, and said method further comprises the steps of:

removing said sample reservoir; and injecting flush solvent from said flush reservoir through said flush valve, solvent selector valve, injection valve and needle in said second direction with said solvent syringe and said sample syringe to purge said components of said sample therefrom.

11. The method of claim 10 wherein said solvent syringe and said sample syringe connect to said flush valve, such that when said flush valve is in said first position a portion of said flush solvent may be drawn into said sample syringe, and when said flush valve is in said second position a portion of said flush solvent may be drawn into said solvent syringe, and wherein said step of injecting flush solvent comprises:

performing, at least once, the steps of:

drawing a portion of said flush solvent into said sample syringe;

switching said flush valve to said second position, and injecting said flush solvent through said flush valve in said second direction with said sample syringe; and performing, at least once, the further steps of:
drawing a portion of said flush solvent into said solvent syringe;
switching said flush valve to said first position, and injecting said flush solvent through said flush valve in said second direction with said solvent syringe.

12. The method of claim 1 wherein said steps are performed under the control of a processor means.

13. An apparatus for automatic preparation of samples from a plurality of components for analysis, said apparatus comprising:
a solvent selector valve having a plurality of ports and a plurality of positions corresponding to ones of said ports, at least some of said plurality of ports being connected to separate solvent reservoirs so that selection may be made therebetween;
a flush valve having a plurality of ports and two positions, and interconnected with said solvent selector valve;
a solvent syringe communicating with a port of said flush valve, and first drive means for operating said solvent syringe;
a sample syringe having a smaller volume than said solvent syringe and connected to a port of said flush valve, and second drive means for operating said sample syringe;
a sample line extending from a port of said flush valve;
a needle disposed at the end of said sample line for insertion into a container;
means for positioning sequentially ones of a plurality of containers at said needle; and
processor means for controlling the operation of said solvent selector valve, flush valve, first and second drive means, and means for positioning, to automatically prepare a sample in a container.

14. The apparatus of claim 13 wherein said solvent syringe is connected to a port of said flush valve, such that said solvent syringe communicates through said flush valve with a port of said solvent selector valve when said flush valve is in at least one position.

15. The apparatus of claim 14 wherein:
the flush valve in its first position connects the solvent syringe to one port of the solvent selector valve and connects the sample line to another port of the solvent selector valve such that said solvent syringe controls the flow in said sample line; and
the flush valve in its second position connects the sample syringe to said sample line and disconnects the sample line from the solvent selector valve, such that said sample syringe controls the flow in said sample line.

16. The apparatus of claim 13 further comprising a solvent loop connected to a port of said solvent selector valve through which said solvent syringe communicates with said solvent selector valve, said solvent loop having a volume greater than the volume of said solvent syringe.

17. The apparatus of claim 13 wherein said solvent selector valve has a main port communicating with said solvent syringe, and at least four additional ports for which corresponding valve positions connect ones of said additional ports to said main port.

18. The apparatus of claim 17 wherein:
said solvent syringe is connected to a port of said flush valve, such that said solvent syringe communicates through said flush valve with said main port of said solvent selector valve; and
said main port and a first port of said solvent selector valve are connected to separate ports of said flush valve, a second port of said solvent selector valve is connected to air, and the remaining ports of said solvent selector valve are connected to separate solvent reservoirs so that selection may be made therebetween.

19. The apparatus of claim 13 further comprising a two-position, six port injection valve disposed in said sample line, and a sample loop extending between two ports of said six port injection valve, and wherein two ports are connected to said sample line, and two ports are dedicated for connection to an analysis device.

20. The apparatus of claim 19 wherein:
with said injection valve in a first position, said sample line remains connected to itself, and said sample loop is connected to said two ports dedicated for connection to an analysis device; and
with said injection valve in a second position, said sample line is connected to said sample loop and said two ports dedicated for connection to an analysis device are connected to each other.

21. The apparatus of claim 19 further comprising an analysis device connected to said two ports dedicated to an analysis device.

22. The apparatus of claim 21 wherein said analysis device is a liquid chromatograph.

23. The apparatus of claim 13 further comprising a flush solvent line extending from a port of said flush valve for connection to a flush solvent reservoir.

24. An apparatus for automatic preparation of samples from a plurality of components for analysis, said apparatus comprising:
a solvent selector valve having a main port, a plurality of additional ports, and a plurality of ports for connection with said main port;
a flush valve having a plurality of ports and two positions, and interconnected with said solvent selector valve;
a solvent syringe connected to a port of said flush valve, and first drive means for operating said solvent syringe;
a sample syringe having a smaller volume than said solvent syringe and connected to a port of said flush valve, and second drive means for operating said sample syringe;
a sample line extending from a port of said flush valve;
a needle disposed at the end of said sample line for insertion into a container;
means for positioning sequentially ones of a plurality of containers at said needle;
a flush solvent line extending from a port of said flush valve for connection to a flush solvent reservoir;
processor means for controlling the operation of said solvent selector valve, flush valve, first and second drive means, and mans for positioning, to automatically prepare a sample in a container, and thereafter automatically purge said components of said sample therefrom;
wherein said flush valve in its first position connects the solvent syringe to the solvent selector valve, such that said solvent syringe can control the flow in said sample line by exerting hydraulic pressure through said flush valve and said solvent selector valve;

wherein said flush valve in its second position connects the sample syringe to said sample line and disconnects the sample line from the solvent selector valve and sample line, such that the sample syringe can control the flow in said sample line; and wherein, interconnecting said flush valve to said solvent selector valve, said apparatus further comprises:

a solvent loop having a volume greater than the volume of said solvent syringe, said solvent loop connecting a port of said flush valve to said main port of said solvent selector valve; and a solvent loop connecting one additional port of said solvent selector valve and one port of said flush valve.

25. The apparatus of claim 24 further comprising an injection valve disposed in said sample line, and an analysis device connected to said injection valve.

* * * * *